(12) United States Patent
Ftouni et al.

(10) Patent No.: US 12,006,286 B2
(45) Date of Patent: Jun. 11, 2024

(54) METHOD FOR TRANSESTERIFICATION OF CARBOXYLIC ACID ESTERS

(71) Applicant: OMYA INTERNATIONAL AG, Oftringen (CH)

(72) Inventors: Jamal Ftouni, Zofingen (CH); Matthias Welker, Hésingue (FR); Samuel Rentsch, Spiegel bei Bern (CH)

(73) Assignee: OMYA INTERNATIONAL AG, Oftringen (CH)

( * ) Notice: Subject to any disclaimer, the term of this patent is extended or adjusted under 35 U.S.C. 154(b) by 181 days.

(21) Appl. No.: 16/981,858

(22) PCT Filed: Mar. 19, 2019

(86) PCT No.: PCT/EP2019/056826
§ 371 (c)(1),
(2) Date: Sep. 17, 2020

(87) PCT Pub. No.: WO2019/180012
PCT Pub. Date: Sep. 26, 2019

(65) Prior Publication Data
US 2021/0122696 A1   Apr. 29, 2021

(30) Foreign Application Priority Data
Mar. 23, 2018  (EP) ..................... 18163580

(51) Int. Cl.
*B01J 23/02*  (2006.01)
*B01J 35/40*  (2024.01)
(Continued)

(52) U.S. Cl.
CPC .............. *C07C 67/03* (2013.01); *B01J 23/02* (2013.01); *B01J 35/40* (2024.01); *B01J 35/50* (2024.01);
(Continued)

(58) Field of Classification Search
None
See application file for complete search history.

(56) References Cited

U.S. PATENT DOCUMENTS

2004/0020410 A1   2/2004   Gane et al.

FOREIGN PATENT DOCUMENTS

CN    102824903 A   12/2012
CN    103977781 A    8/2014
(Continued)

OTHER PUBLICATIONS

Wang et al. (A facile, low-cost route for the preparation of calcined porous calcite and dolomite and their application as heterogeneous catalysts in biodiesel production, Catalysis Science and Technology, 3, pp. 2244-2251, published 2013) (Year: 2013).*
(Continued)

*Primary Examiner* — Sheng H Davis
*Assistant Examiner* — Keling Zhang
(74) *Attorney, Agent, or Firm* — Heslin Rothenberg Farley & Mesiti, P.C.

(57) ABSTRACT

The present invention relates to a method for transesterification of carboxylic acid esters by heterogeneous catalysis using a catalyst that is obtainable by calcination of surface-reacted calcium carbonate. The invention further relates to the use of said method in the production of fuel or fuel components, such as biodiesel. Further aspects of the present invention relate to the transesterified ester obtainable by the inventive method and to its use as fuel or as fuel component. Still another aspect of the present invention relates to a corresponding transesterification catalyst and to its use in transesterification reactions.

18 Claims, 4 Drawing Sheets

(51) Int. Cl.
  *B01J 35/50* (2024.01)
  *B01J 35/61* (2024.01)
  *B01J 37/08* (2006.01)
  *C07C 67/03* (2006.01)

(52) U.S. Cl.
  CPC ........... *B01J 35/613* (2024.01); *B01J 35/615* (2024.01); *B01J 37/088* (2013.01)

(56) References Cited

FOREIGN PATENT DOCUMENTS

| EP | 2189214 | A1 | | 5/2010 |
|---|---|---|---|---|
| EP | 2264108 | A1 | | 12/2010 |
| EP | 2264109 | A1 | | 12/2010 |
| EP | 2371766 | A1 | | 10/2011 |
| EP | 2447213 | A1 | | 5/2012 |
| EP | 2524898 | A1 | | 11/2012 |
| EP | 2840065 | A1 | | 2/2015 |
| EP | 3176222 | A1 | | 6/2017 |
| EP | 3275537 | A1 | * | 1/2018 |
| JP | 5186606 | B1 | | 4/2013 |
| WO | 0039222 | A1 | | 7/2000 |
| WO | 2004083316 | A1 | | 9/2004 |
| WO | 2005121257 | A2 | | 12/2005 |
| WO | 2006134845 | A1 | | 12/2006 |
| WO | 2009074492 | A1 | | 6/2009 |
| WO | 2013142473 | A1 | | 9/2013 |

OTHER PUBLICATIONS

Cho et al., High activity of acid-treated quail eggshell catalysts in the transesterification of palm oil with methanol, Bioresource Technology, 2010, 8515-8519 (Year: 2010).*

Verziu et al., Transesterification of vegetable oils over CaO catalysts, Catalysis Today, 2011, 64-70 (Year: 2011).*

International Search Report and Written Opinion issued in PCT/EP2019/056826 mailed Jun. 5, 2019.

Rui Wang et al., "A facile, low-cost route for the preparation of calcined porous calcite and dolomite and their application as heterogeneous catalysts in biodiesel production," Catalysis Science & Technology, vol. 3, No. 9, Jan. 1, 2013, pp. 2244-2251.

* cited by examiner

METHOD FOR TRANSESTERIFICATION OF CARBOXYLIC ACID ESTERS

CROSS REFERENCE TO RELATED APPLICATIONS

This application is a U.S. National Phase filing under 35 U.S.C. § 371 of International Application PCT/EP2019/056826, filed Mar. 19, 2019, and published as WO 2019/180012 A1 and corrected publication WO 2019/180012 A9 on Sep. 26, 2019. PCT/EP2019/056826 claims priority from European patent application number 18163580.6, filed Mar. 23, 2018. The entire contents of each of these prior applications are hereby incorporated herein by reference.

The present invention relates to a method for transesterification of carboxylic acid esters by heterogeneous catalysis using a catalyst that is obtainable by calcination of surface-reacted calcium carbonate. The invention further relates to the use of said method in the production of fuel or fuel components, such as biodiesel. Further aspects of the present invention relate to the transesterified ester obtainable by the inventive method and to its use as fuel or as fuel component. Still another aspect of the present invention relates to a corresponding transesterification catalyst and to its use in transesterification reactions.

Transesterification is the process of exchanging the organic group R'' of an ester with the organic group R' of an alcohol according to the following reaction scheme:

$$R''O(O\!\!=\!\!)CR + R'OH \rightarrow R'O(O\!\!=\!\!)CR + R''OH$$

This type of reaction is applied in a number of large scale industrial processes. For example, the synthesis of polyesters can be achieved through transesterification of diesters with diols. During the last decades, transesterification of fats (constituted of triglycerides) has gained importance in the production of non-fossil fuels, especially biodiesel.

The term biodiesel refers to a vegetable or animal fat-based fuel which can be obtained by chemically reacting these fats with an alcohol to produce fatty acid esters. Methanol is most frequently used as the alcohol which yields fatty acid methyl esters (so called FAMEs). In case of fat transesterification, glycerine is obtained as a marketable by-product.

Typically, transesterifications are carried out in the presence of a suitable catalyst, which can be either a base catalyst or an acid catalyst. Commonly used base catalysts include sodium hydroxide (NaOH), potassium hydroxide (KOH) or sodium methoxide ($H_3CONa$). In turn, commonly used acid catalysts include sulphuric acid ($H_2SO_4$) and phosphoric acid ($H_3PO_4$).

Particular demands with respect to transesterification methods are full conversion, high reaction rates and the prevention of unwanted impurities. Unwanted impurities of transesterification processes include, for example, salts of the carboxylic acid.

In general, acid catalysts are known to work less efficient compared to base catalysts and the transesterification process requires large quantities of excess alcohol. The formation of water during transesterification can further reduce the reaction rate or it can even stop the reaction. Usually, strong acids (e.g. sulphuric acid) are required to achieve full conversion at high reaction rates which, in turn, requires the use of acid-resistant equipment.

Conversely, the use of known base catalysts, such as sodium hydroxide or potassium hydroxide, also has disadvantages. In this regard, formation of carboxylic acid salts is one major issue. In case of fat transesterification, these carboxylic acid salts are fatty acid salts that act as soaps and may cause problems at several stages of the process. A subsequent washing step may thus be required.

Sodium hydroxide (NaOH) is a cheap and readily available catalyst, but handling and dissolving of sodium hydroxide is difficult and hazardous. Potassium hydroxide (KOH) dissolves more easily, but is more expensive and more sensitive towards moisture upon storage.

Finally, removal of the catalyst itself is also an issue, in particular in case of soluble catalysts like NaOH or KOH. As mentioned above, the catalyst may be present as or lead to the formation of impurities in the ester product. Depending on the substrate, i.e. the starting material, impurities in marketable by-products (e.g. in glycerine in case of fat transesterification) are also problematic.

There exists a general need to overcome one or more of the foregoing drawbacks or to improve the methods described hereinabove.

Thus, one object of the present invention can be seen in the provision of a transesterification method, wherein the catalyst can be separated easily from the reaction mixture.

Another object can be seen in the provision of a more efficient transesterification method or in the provision of a corresponding catalyst.

Still another object of the present invention can be seen in the reduction of process impurities and in the provision of a corresponding catalyst.

Still another object can be seen in the provision of a transesterification method that can be handled easily and in the provision of a corresponding catalyst that can be stored or used easily and safely. Environmental compatibility of the method or the catalyst can be seen as another object of the present invention.

Finally, still another object of the present invention can be seen in the provision of a more economical catalyst system for use in transesterification reactions.

The foregoing and other problems can be solved by the subject-matter as defined herein in the independent claims.

In this regard, a first aspect of the present invention relates to a method for transesterification of carboxylic acid esters by heterogeneous catalysis, the method comprising the following steps:

(a) providing a substrate comprising a first carboxylic acid ester;
(b) providing a first alcohol;
(c) providing a catalyst; and
(d) reacting the substrate provided in step (a) and the first alcohol provided in step (b) in the presence of the catalyst provided in step (c) to obtain a reaction mixture comprising a second carboxylic acid ester and a second alcohol;
characterized in that the catalyst comprises calcined surface-reacted calcium carbonate, wherein the surface-reacted calcium carbonate is a reaction product of ground natural calcium carbonate-containing mineral (GNCC) or precipitated calcium carbonate (PCC) with carbon dioxide and one or more $H_3O^+$ ion donors and wherein the carbon dioxide is formed in situ by the $H_3O^+$ ion donors treatment and/or is supplied from an external source.

The inventors have found, surprisingly, that the use of a catalyst comprising calcined surface-reacted calcium carbonate leads to an efficient transesterification. As will be explained in more detail hereinbelow, surface-reacted calcium carbonate is a specific type of calcium carbonate obtained by reacting a calcium carbonate-containing material, carbon dioxide and one or more $H_3O^+$ ion donors. Prior to its use, the catalyst is activated by subsequent calcination at elevated temperatures. Furthermore, the inventors have surprisingly found that the use of a catalyst comprising calcined surface-reacted calcium carbonate leads to a reduction of impurities.

Another aspect of the present invention relates to the use of the inventive method in the production of fuel or fuel components.

Still another aspect of the present invention relates to a carboxylic acid ester obtainable by the inventive method.

Still another aspect relates to the use of a carboxylic acid ester obtainable by the inventive method as fuel or as a fuel component.

Still another aspect relates to a transesterification catalyst comprising calcined surface-reacted calcium carbonate,
wherein the surface-reacted calcium carbonate is a reaction product of ground natural calcium carbonate containing mineral (GNCC) or precipitated calcium carbonate (PCC) with carbon dioxide and one or more $H_3O^+$ ion donors and wherein the carbon dioxide is formed in situ by the $H_3O^+$ ion donors treatment and/or is supplied from an external source.

Finally, still another aspect of the present invention relates to the use of a catalyst comprising calcined surface-reacted calcium carbonate as catalyst in a transesterification reaction,
wherein the surface-reacted calcium carbonate is a reaction product of ground natural calcium carbonate containing mineral (GNCC) or precipitated calcium carbonate (PCC) treated with carbon dioxide and one or more $H_3O^+$ ion donors and wherein the carbon dioxide is formed in situ by the $H_3O^+$ ion donors treatment and/or is supplied from an external source.

The following terms used throughout this document shall have the meanings as set forth hereinafter.

As already explained hereinabove, "surface-reacted calcium carbonate" is a specific type of calcium carbonate. It is obtained by the reaction of ground natural calcium carbonate-containing mineral (GNCC) or precipitated calcium carbonate (PCC) with carbon dioxide and one or more $H_3O^+$ ion donors, wherein the carbon dioxide is formed in situ by the $H_3O^+$ ion donors treatment and/or is supplied from an external source.

The term "calcined" as used herein refers to the appearance of a solid material that has been subjected to calcination. Calcination denotes a thermal treatment at elevated temperatures in the presence or in the absence of oxygen, preferably in the presence of oxygen, for example atmospheric oxygen. The terms "calcined" and "calcination" are well known to the skilled person and it is understood that calcination can lead to partial of full thermal conversion of the starting material (partial or full calcination).

The term "ground natural calcium carbonate" (GNCC) in the meaning of the present document refers to a particulate material obtained from natural calcium carbonate-containing minerals (e.g. chalk, limestone, marble or dolomite) which has been processed in a wet and/or dry comminution step, such as crushing and/or grinding, and optionally has been subjected to further steps such as screening and/or fractionation, for example, by a cyclone or a classifier.

A "precipitated calcium carbonate" (PCC) is a synthesized material, obtained by precipitation following a reaction of carbon dioxide and calcium hydroxide (hydrated lime) in an aqueous environment. Alternatively, precipitated calcium carbonate can also be obtained by reacting calcium- and carbonate salts, for example calcium chloride and sodium carbonate, in an aqueous environment. PCC may have a vateritic, calcitic or aragonitic crystalline form. PCCs are described, for example, in EP 2 447 213 A1, EP 2 524 898 A1, EP 2 371 766 A1, EP 2 840 065 A1, or WO 2013/142473 A1.

Where used herein, the volume-based particle size distribution $d_x(vol)$ represents the diameter relative to which x % by volume of the particles have diameters less than $d_x(vol)$. This means that, for example, the $d_{20}(vol)$ value is the particle size at which 20 vol. % of all particles are smaller than that particle size. The $d_{50}(vol)$ value is thus the volume median particle size, i.e. 50 vol. % of all particles are smaller than that particle size and the $d_{98}(vol)$ value, referred to as volume-based top cut, is the particle size at which 98 vol. % of all particles are smaller than that particle size.

In turn, the weight-based particle size distribution $d_x(wt)$ represents the diameter relative to which x % by weight of the particles have diameters less than $d_x(wt)$. This means that, for example, the $d_{20}(wt)$ value is the particle size at which 20 wt. % of all particles are smaller than that particle size. The $d_{50}(wt)$ value is thus the weight median particle size, i.e. 50 wt. % of all particles are smaller than that particle size and the $d_{98}(wt)$ value, referred to as weight-based top cut, is the particle size at which 98 wt. % of all particles are smaller than that particle size.

Throughout the present document, the term "specific surface area" (in $m^2/g$), which is used to define surface-reacted calcium carbonate or other materials, refers to the specific surface area as determined by using the BET method (using nitrogen as adsorbing gas).

Where an indefinite or definite article is used when referring to a singular noun, e.g. "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

Advantageous embodiments of the inventive method and the further aspects are defined in the corresponding sub-claims.

In one embodiment of the present invention, the substrate is a fat or a fatty oil, preferably a vegetable oil, more preferably the substrate is selected from the group consisting of canola oil, cottonseed oil, coconut oil, corn oil, hazelnut oil, linseed oil, mustard seed oil, olive oil, palm oil, peanut oil, rapeseed oil, rice bran oil, safflower oil, sesame oil, soybean oil, sunflower oil, tiger nut oil, tung oil and mixtures thereof, and most preferably the substrate is sunflower oil.

In another embodiment of the inventive method, the first carboxylic acid ester is a triglyceride.

In still another embodiment, the first alcohol is a monohydric alcohol, preferably a monohydric $C_1$-$C_5$ alcohol, more preferably a monohydric $C_1$-$C_3$ alcohol, still more preferably methanol or ethanol, and most preferably methanol.

In another embodiment of the present invention, the catalyst has:
(i) a $d_{50}$(vol) of from 1 to 75 µm, preferably from 1.5 to 50 µm, more preferably from 2 to 30 µm, and most preferably from 3 to 15 µm; and/or
(ii) a $d_{98}$(vol) of from 2 to 150 µm, preferably from 5 to 120 µm, more preferably from 8 to 80 µm, and most preferably from 10 to 30 µm.

In still another embodiment, the catalyst has a specific surface area of from 1 to 200 $m^2/g$, preferably from 5 to 120 $m^2/g$, and most preferably from 10 to 100 $m^2/g$, measured using nitrogen and the BET method according to ISO 9277:2010.

In still another embodiment, the surface-reacted calcium carbonate has:
(i) a $d_{50}$(vol) of from 0.5 to 50 µm, preferably from 1 to 30 µm, more preferably from 1.5 to 20 µm, and most preferably from 2 to 12 µm; and/or
(ii) a $d_{98}$(vol) of from 1 to 120 µm, preferably from 2 to 100 µm, more preferably from 5 to 50 µm, and most preferably from 8 to 25 µm.

In still another embodiment, the surface-reacted calcium carbonate has a specific surface area of from 15 to 200 $m^2/g$, preferably from 25 to 180 $m^2/g$, and most preferably from 30 to 150 $m^2/g$, measured using nitrogen and the BET method according to ISO 9277:2010.

In another embodiment, the catalyst is characterized in that:
(i) the ground natural calcium carbonate-containing mineral is selected from the group consisting of marble, chalk, dolomite, limestone and mixtures thereof; and/or
(ii) the precipitated calcium carbonate comprises aragonitic, vateritic or calcitic mineralogical crystal forms or mixtures thereof.

In still another embodiment of the present invention, the catalyst is obtainable by partial or full calcination of surface-reacted calcium carbonate.

In another embodiment, the catalyst is obtainable by calcination of surface-reacted calcium carbonate, wherein calcination is carried out:
(i) at a calcination temperature of at least 650° C., preferably at least 680° C., and most preferably at a temperature of from 700 to 950° C.; and/or
(ii) at a calcination time of at least 5 min, preferably at least 0.25 hours, more preferably at least 0.5 hours, and most preferably at a calcination time of from 1 to 3 hours.

In another embodiment, the method is characterized in that in step (d), the first alcohol is used as reaction medium, preferably said first alcohol is used in molar excess relative to the first carboxylic acid ester.

In another embodiment, the method is characterized in that in step (d), the catalyst is used in an amount of from 0.01 to 20 wt. %, preferably from 0.1 to 10 wt. %, and most preferably from 0.5 to 5 wt. %, based on the total weight of the substrate.

In still another embodiment, the method is characterized in that in step (d), the alcohol and the catalyst are contacted in a first step and the substrate is then added in a second step.

In still another embodiment, the method is characterized in that step (d) is carried out at a temperature of at least 20° C., preferably at least 25° C., and most preferably at a range of from 30 to 80° C.

In still another embodiment, the method further comprises step (e) of separating the second carboxylic acid ester from the reaction mixture obtained in step (d).

In the following, details and preferred embodiments of the transesterification method according to the present invention will be disclosed. It is to be understood that these details and embodiments, where applicable, also refer to the use of the inventive method in the production of fuel or fuel components, to the carboxylic acid ester obtainable by said inventive method and to the use of said ester as fuel or as a fuel component. Where applicable, the following details and embodiments further refer to the inventive transesterification catalyst and to the use of said catalyst as a catalyst in transesterification reactions.

(A) Substrate

According to step (a) of the inventive transesterification method, a substrate is provided which comprises a first carboxylic acid ester that is reacted with the first alcohol provided in step (b). The term "first carboxylic acid ester" denotes that the ester of the substrate and the ester product, i.e. the "second carboxylic acid ester", have a different chemical structure.

In principle, the first carboxylic acid ester used in the present invention can be any organic molecule provided that it features one or more ester moieties which can be generally described as R"O(O=)CR, wherein R" and R may be the same or different and may be any conceivable organic radical.

In this regard, the first carboxylic acid ester can be a monoester, i.e. an organic molecule featuring one ester moiety, or it can be a diester, a triester etc., i.e. an organic molecule featuring two or more ester moieties. In case the first carboxylic acid ester comprises two or more ester moieties, this particularly refers to polyesterified polyhydric alcohols (e.g. a diglyceride or a triglyceride).

Particularly suitable esters are glycerides, preferably triglycerides, which are the constituents of (solid) fats or (liquid) fatty oils, collectively referred to as natural "fats", wherein a further distinction can be made between saturated and non-saturated fats. Therefore, in one embodiment, the substrate is a fat or a fatty oil, preferably a fatty oil. In a more preferred embodiment, the substrate is a vegetable oil, still more preferably selected from the group consisting of canola oil, cottonseed oil, coconut oil, corn oil, hazelnut oil, linseed oil, mustard seed oil, olive oil, palm oil, peanut oil, rapeseed oil, rice bran oil, safflower oil, sesame oil, soybean oil, sunflower oil, tiger nut oil, tung oil and mixtures thereof, most preferably the substrate is sunflower oil.

Especially in case of fats, e.g. fatty oils, the substrate can be a fresh substrate or a used substrate, i.e. a used fatty oil. In this regard, the inventive method can further be used for the treatment or conversion of used fats.

As noted above, the substrate comprises a first carboxylic acid ester which can have the general formula R"O(O=)CR. In one embodiment of the present invention, the first carboxylic acid ester is a glyceride, preferably a triglyceride. The skilled person will recognize that the substrate can comprise a mixture of two or more structurally different carboxylic acid esters, e.g. different triglycerides as in case of natural fats. The simplest triglycerides are those where the three fatty acids are identical. In turn, a polyesterified polyhydric alcohol, such as a triglyceride, can be substituted with different acyl radicals.

(B) Alcohol

In step (b) of the method according to the present invention, a first alcohol is provided. The term "first alcohol" denotes that the alcohol provided as a reactant in step (b) and the alcohol product, i.e. the "second alcohol", have a different chemical structure.

In principle, the first alcohol used in the present invention can be any organic alcohol provided that it features at least one hydroxy group. The alcohol thus can be generally described as R'OH, wherein R' may be any conceivable organic radical. In particular, the first alcohol provided in step (b) can be a monohydric alcohol, meaning that it contains only one hydroxy group.

Therefore, in one embodiment of the present invention, the first alcohol is a monohydric alcohol, preferably a monohydric $C_1$-$C_5$ alcohol, and more preferably a monohydric $C_1$-$C_3$ alcohol. For example, $C_1$-$C_5$ denotes a substituted or unsubstituted linear or branched alkyl chain having from 1 to 5 carbon atoms. Non-limiting examples of suitable monohydric alcohols thus include the structural isomers of pentanol, the structural isomers of butanol, n-propyl alcohol, isopropyl alcohol, ethanol and methanol. In another preferred embodiment, the first alcohol provided in step (b) is selected from n-propyl alcohol, isopropyl alcohol, ethanol and methanol, still more preferably methanol or ethanol, and most preferably the first alcohol is methanol.

(C) Catalyst

The catalyst of the inventive method provided in step (c) comprises surface-reacted calcium carbonate activated by calcination, wherein the surface-reacted calcium carbonate is a reaction product of ground natural calcium carbonate-containing mineral (GNCC) or precipitated calcium carbonate (PCC) with carbon dioxide and one or more $H_3O^+$ ion donors and wherein the carbon dioxide is formed in situ by the $H_3O^+$ ion donors treatment and/or is supplied from an external source.

The base material of the activated catalyst is a surface-reacted calcium carbonate (SRCC) which is also referred to as modified calcium carbonate (MCC).

It is appreciated that the surface-reacted calcium carbonate can be one or a mixture of different kinds of surface-reacted calcium carbonate(s). In one embodiment of the present invention, the surface-reacted calcium carbonate comprises, preferably consists of, one kind of surface-reacted calcium carbonate. Alternatively, the surface-reacted calcium carbonate comprises, preferably consists of, two or more kinds of surface-reacted calcium carbonates. For example, the surface-reacted calcium carbonate comprises, preferably consists of, two or three kinds of surface-reacted calcium carbonates. Preferably, the surface-reacted calcium carbonate comprises, more preferably consists of, one kind of surface-reacted calcium carbonate.

The surface-reacted calcium carbonate is a reaction product of ground natural calcium carbonate (GNCC) or precipitated calcium carbonate (PCC) treated with carbon dioxide and one or more $H_3O^+$ ion donors, wherein the carbon dioxide is formed in situ by the $H_3O^+$ ion donors treatment and/or is supplied from an external source. Because of the reaction of ground natural calcium carbonate or precipitated calcium carbonate with carbon dioxide and the one or more $H_3O^+$ ion donors, surface-reacted calcium carbonate may comprise GNCC or PCC and at least one water-insoluble calcium salt other than calcium carbonate.

In a preferred embodiment, said surface-reacted calcium carbonate comprises GNCC or PCC and at least one water-insoluble calcium salt other than calcium carbonate which is present on at least part of the surface of said GNCC or PCC.

An $H_3O^+$ ion donor in the context of the present invention is a Brønsted acid and/or an acid salt.

In a preferred embodiment of the invention, the surface-reacted calcium carbonate is obtained by a process comprising the steps of:
(a) providing a suspension of ground natural calcium carbonate (GNCC) or precipitated calcium carbonate (PCC);
(b) adding at least one acid having a $pK_a$ value of 0 or less at 20° C., or having a $pK_a$ value from 0 to 2.5 at 20° C. to the suspension provided in step (a); and
(c) treating the suspension provided in step (a) with carbon dioxide before, during or after step (b).

According to another embodiment, the surface-reacted calcium carbonate is obtained by a process comprising the steps of:
(a) providing a ground natural calcium carbonate (GNCC) or precipitated calcium carbonate (PCC);
(b) providing at least one water-soluble acid;
(c) providing gaseous carbon dioxide; and
(d) contacting said GNCC or PCC provided in step (a), the at least one acid provided in step (b) and the gaseous carbon dioxide provided in step (c);
characterized in that
(i) the at least one acid provided in step (b) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt; and
(ii) following contacting the at least one water-soluble acid provided in step (b) and the GNCC or PCC provided in step (a), at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

The source of calcium carbonate, e.g., ground natural calcium carbonate (GNCC), preferably is selected from calcium carbonate-containing minerals selected from the group comprising marble, chalk, limestone and mixtures thereof. Natural calcium carbonate may comprise further naturally occurring components such as magnesium carbonate, alumino silicate etc. According to one embodiment, natural calcium carbonate, such as GNCC, comprises aragonitic, vateritic or calcitic mineralogical crystal forms of calcium carbonate or mixtures thereof.

In general, the grinding of ground natural calcium carbonate may be performed in a dry or wet grinding process and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulverizer, a shredder, a de-clumper, a knife cutter, or other such equipment known to the skilled person. In case the ground natural calcium carbonate comprises wet ground calcium carbonate, the grinding step may be performed under conditions such that autogenous grinding takes place and/or by horizontal ball milling, and/or other such processes known to the skilled person. The wet processed ground natural calcium carbonate thus obtained may be washed and dewatered by well-known processes, e.g., by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

As already indicated hereinabove, a precipitated calcium carbonate (PCC) in the meaning of the present invention is a synthesized material, generally obtained by precipitation following a reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained aqueous PCC slurry can be mechanically dewatered and dried.

According to one embodiment of the present invention, the precipitated calcium carbonate comprises aragonitic, vateritic or calcitic mineralogical crystal forms of calcium carbonate or mixtures thereof.

Precipitated calcium carbonate may be ground prior to the treatment with carbon dioxide and at least one $H_3O^+$ ion donor by the same means as used for grinding natural calcium carbonate and described above.

According to one embodiment of the present invention, the natural or precipitated calcium carbonate is in form of particles having a weight median particle size $d_{50}(wt)$ of from 0.05 to 10.0 μm, preferably from 0.2 to 5.0 μm, more preferably from 0.4 to 3.0 μm, most preferably from 0.6 to 1.2 μm, and especially 0.7 μm. According to a further embodiment of the present invention, the natural or precipitated calcium carbonate is in form of particles having a top cut particle size $d_{98}(wt)$ of from 0.15 to 55 μm, preferably from 1 to 40 μm, more preferably from 2 to 25 μm, most preferably from 3 to 15 μm, and especially 4 μm.

The natural or precipitated calcium carbonate may be used dry or suspended in water. Preferably, a corresponding aqueous slurry has a content of natural or precipitated calcium carbonate within the range of from 1 to 90 wt. %, more preferably from 3 to 60 wt. %, even more preferably from 5 to 40 wt. %, and most preferably from 10 to 25 wt. %, based on the total weight of said slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralized by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to a more preferred embodiment, the weak acid has a $pK_a$ value from greater than 2.5 to 5 at 20° C., and more preferably the weak acid is selected from the group consisting of acetic acid, formic acid, propanoic acid and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of dropwise addition, this addition preferably takes place within a time period of 10 min. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralized by a corresponding cation such as $Li^+$, $Na^+$ or $K^+$, $HPO_4^{2-}$, being at least partially neutralized by a corresponding cation such as $Li^+$, $Na^+$, $K^+$, $Mg^{2+}$ or $Ca^{2+}$ and mixtures thereof, more preferably the at least one acid is selected from the group consisting of hydrochloric acid, sulphuric acid, sulphurous acid, phosphoric acid, oxalic acid, or mixtures thereof. A particularly preferred $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

In another preferred embodiment, the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, wherein the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

In a particularly preferred embodiment, the at least one $H_3O^+$ ion donor is a mixture of phosphoric acid and citric acid, more preferably the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1. In this embodiment, phosphoric acid is preferably used in excess relative to citric acid.

As an alternative, it is also possible to add the $H_3O^+$ ion donor to the water before the natural or precipitated calcium carbonate is suspended.

In a next step, the natural or precipitated calcium carbonate is treated with carbon dioxide. If a strong acid such as sulphuric acid or hydrochloric acid is used for the $H_3O^+$ ion donor treatment of the natural or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g., with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous carbon dioxide) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present document.

Similarly, surface-reacted precipitated calcium carbonate may be obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counter ion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural or precipitated calcium carbonate, the natural or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, aluminium sulphate or mixtures thereof. Preferably, the at least one silicate is selected from an aluminium silicate, a calcium silicate, or an earth alkali metal silicate.

In another preferred embodiment, said at least one compound is aluminium sulphate hexadecahydrate. In a particularly preferred embodiment, said at least one compound is aluminium sulphate hexadecahydrate, wherein the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, more preferably the molar ratio of said $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

The foregoing components can be added to an aqueous suspension comprising the natural or precipitated calcium carbonate before adding the acid and/or carbon dioxide.

Alternatively, the foregoing components can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present document.

The surface-reacted calcium carbonate can be kept in suspension, optionally further stabilized by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural or precipitated calcium carbonate in the form of granules or a powder.

The surface-reacted calcium carbonate may have different particle shapes, such as e.g., the shape of roses, golf balls and/or brains.

In a preferred embodiment, the surface-reacted calcium carbonate has a specific surface area of from 15 to 200 $m^2/g$, preferably from 25 to 180 $m^2/g$, and most preferably from 30 to 150 $m^2/g$, measured using nitrogen and the BET method according to ISO 9277:2010. In a further embodiment, the surface-reacted calcium carbonate has a specific surface area of 120 $m^2/g$ or less, more preferably from 60 to 120 $m^2/g$, and most preferably from 70 to 105 $m^2/g$, measured using nitrogen and the BET method according to ISO 9277:2010. For example, the surface-reacted calcium carbonate may have a specific surface area of from 75 to 100 $m^2/g$, measured using nitrogen and the BET method according to ISO 9277:2010.

It may furthermore be preferred that the surface-reacted calcium carbonate particles have a volume median grain diameter $d_{50}(vol)$ of from 0.5 to 50 µm, preferably from 1 to 30 µm, more preferably from 1.5 to 20 µm, and most preferably from 2 to 12 µm. According to another preferred embodiment, the surface-reacted calcium carbonate particles have a volume median grain diameter $d_{50}(vol)$ of from 1.5 to 12 µm, preferably from 2 to 5 µm or from 6 to 10 µm.

It may furthermore be preferred that the surface-reacted calcium carbonate particles have a grain diameter $d_{98}(vol)$ of from 1 to 120 µm, preferably from 2 to 100 µm, more preferably from 5 to 50 µm, and most preferably from 8 to 25 µm. According to another preferred embodiment, the surface-reacted calcium carbonate particles have a volume median grain diameter $d_{98}(vol)$ of from 5 to 20 µm, preferably from 8 to 12 µm or from 13 to 18 µm.

According to another embodiment, the surface-reacted calcium carbonate has an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g., 0.004 to 0.50 µm determined by mercury porosimetry measurement.

The catalyst provided in step (c) of the inventive method and used in the subsequent transesterification step (d) is a calcined surface-reacted calcium carbonate, meaning that the catalyst is a material obtainable by calcination of surface-reacted calcium carbonate. As already explained hereinabove, calcination denotes a thermal treatment at elevated temperatures leading to a partial of full thermal conversion of the starting material (partial of full calcination).

Therefore, in one embodiment, the catalyst comprises calcined surface-reacted calcium carbonate which is obtainable by partial or full calcination of surface-reacted calcium carbonate. In the meaning of the present invention, full calcination indicates that the percentage of calcium carbonate ($CaCO_3$) in the calcined substrate as determined by XRD does not decrease (contrary to the case of partial calcination) by more than 1%, based on the total composition, over a period of 15 min at a given calcination temperature. For example, if the initial percentage of calcium carbonate in a calcined sample is 5% determined by XRD, full calcination means that the percentage of calcium carbonate in said sample does not fall below 4% determined by XRD over a period of 15 min at the relevant calcination temperature.

The degree of calcination (partial or full calcination) can influence the activity of the transesterification catalyst which, in turn, can depend on the calcination temperature and the calcination time. Thus, in one embodiment, the catalyst is obtained by partial or full calcination of surface-reacted calcium carbonate, preferably by full calcination.

Additionally, the activation of the catalyst or the degree of calcination can be defined through a specific calcination temperature and/or a specific calcination time. In one embodiment, the catalyst is thus obtainable by calcination of surface-reacted calcium carbonate, wherein calcination is carried out at a calcination temperature of at least 650° C., preferably at least 680° C., and most preferably at a temperature of from 700 to 950° C.; and/or at a calcination time of at least 5 min, preferably at least 0.25 hours, more preferably at least 0.5 hours, and most preferably at a calcination time of from 1 to 3 hours. In a particularly preferred embodiment, the catalyst is obtainable by calcination of surface-reacted calcium carbonate, wherein calcination is carried out at a temperature of from 700 to 950° C. and at a calcination time of from 1 to 3 hours.

Figure 3:
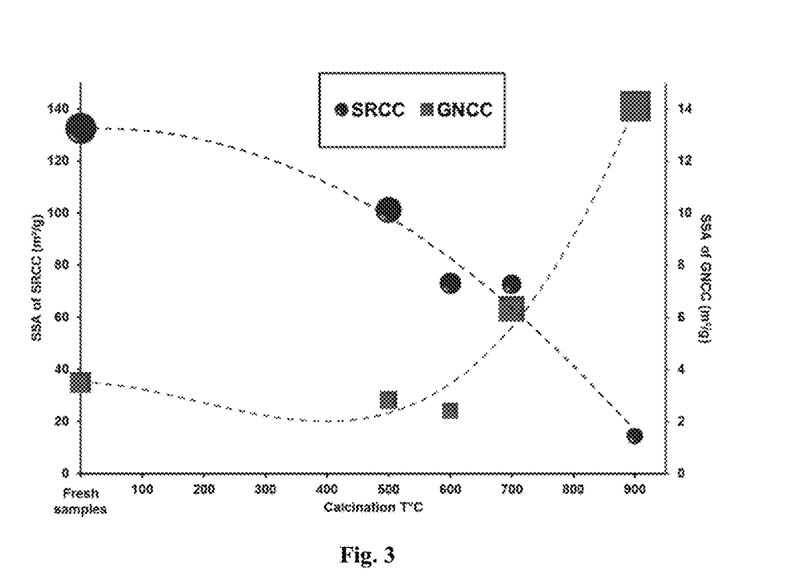
FIG. 3: Evolution of the surface area of ground natural calcium carbonate and surface-reacted calcium carbonate as a function of the activation temperature.

As can be gathered from FIG. 3, the specific surface area of surface-reacted calcium carbonate surprisingly decreases upon thermal activation. This is in contrast to what can be observed in case of conventional ground natural calcium carbonate and the skilled person thus would have expected a poor total conversion or a reduced reaction rate of the transesterification reaction. However, the contrary is true as the comparison of calcined GNCC and calcined SRCC shows that the catalysts perform equally well although the specific surface area is decreased during activation and the lime (CaO) content of the catalyst is comparably low.

Figure 5:
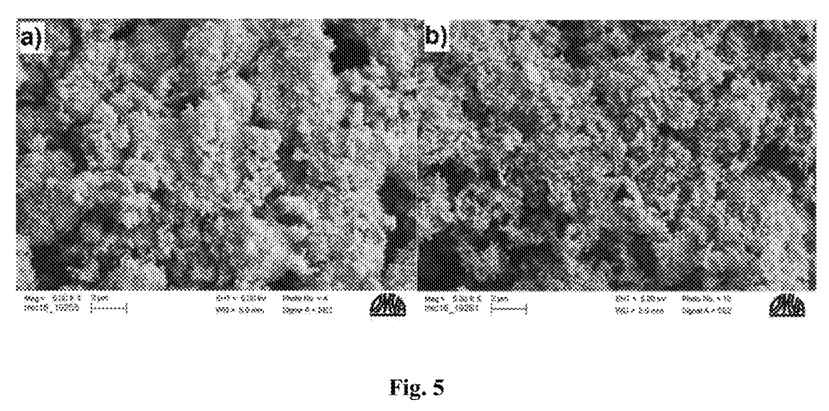
FIG. 5: (a) SEM micrograph of SRCC prior to calcination, (b) SEM micrograph of SRCC calcined at 900° C. for 3 h in a Nabertherm furnace model Le 6/11, Nabertherm GmbH, Lilienthal, Germany.
Figure 6:
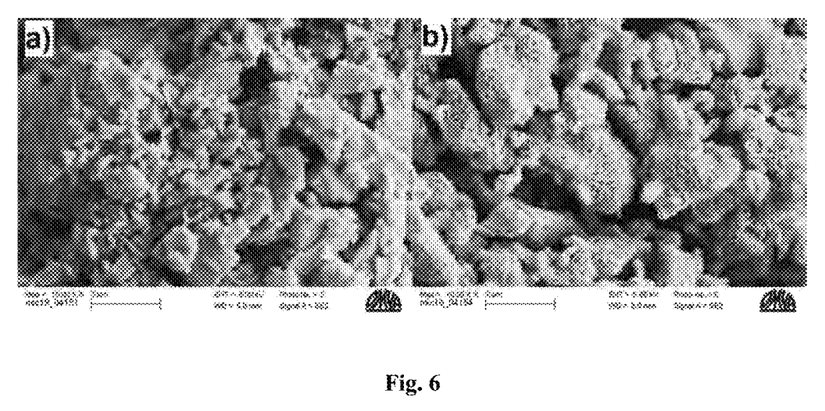
FIG. 6: (a) SEM micrograph of GNCC prior to calcination, (b) SEM micrograph of GNCC calcined at 900° C. for 3 hrs in a Nabertherm furnace model Le 6/11, Nabertherm GmbH, Lilienthal, Germany.
Figure 7:
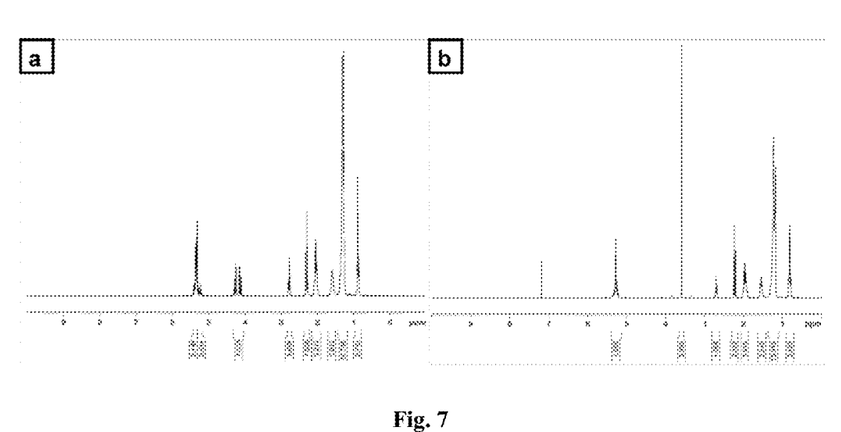
FIG. 7: (a) NMR spectrum of sun flower oil; b) NMR spectrum of transesterification product obtained with GNCC calcined at 900° C.

As can be gathered from FIG. 5, the characteristics of the surface structure of SRCC are essentially retained or only slightly altered upon thermal activation. On the contrary, FIG. 6 shows the formation of micropores upon thermal activation of GNCC.

Specifically, in another embodiment of the present invention, the catalyst has a specific surface area of from 1 to 200 $m^2/g$, preferably from 5 to 120 $m^2/g$, and most preferably from 10 to 100 $m^2/g$, measured using nitrogen and the BET method according to ISO 9277:2010. In still another embodiment, the catalyst can have a specific surface area of from 1 to 120 $m^2/g$, preferably from 3 to 50 $m^2/g$, and most preferably from 5 to 25 $m^2/g$, measured using nitrogen and the BET method according to ISO 9277:2010.

Figure 4:
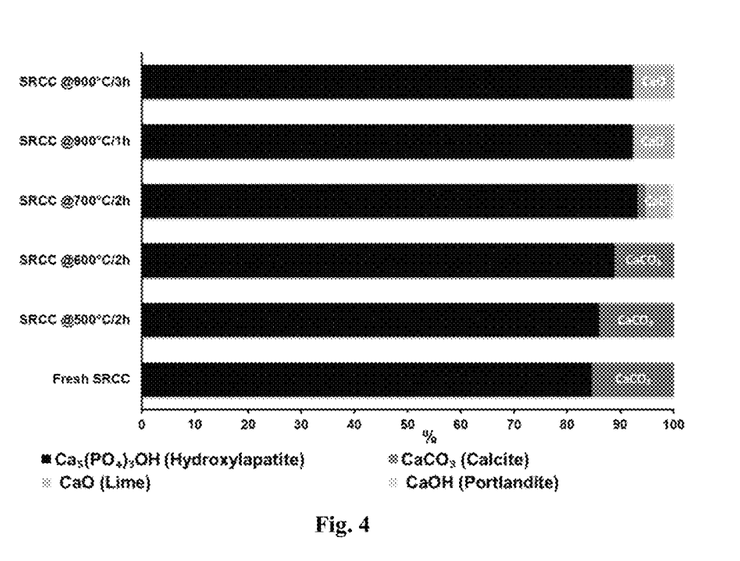
FIG. 4: X-ray diffractograms of surface-reacted calcium carbonate activated thermally at different temperatures and different times of thermal activation.

As regards the lime content, it can be gathered from FIG. 4, that the chemical composition of surface-reacted calcium carbonate changes upon thermal activation. In an exemplary embodiment, the chemical composition of calcined surface-reacted calcium carbonate as determined by XRD comprises: 0.5 to 50% calcium oxide (CaO), 0.5 to 50% calcium carbonate ($CaCO_3$), 70 to 99% hydroxyapatite ($Ca_5(PO_4)_3OH$), and 0 to 5% calcium hydroxide ($Ca(OH)_2$), each based on the total composition.

Additionally or alternatively, in one embodiment of the present invention, the catalyst has a $d_{50}(vol)$ of from 1 to 75 µm, preferably from 1.5 to 50 µm, more preferably from 2 to 30 µm, and most preferably from 3 to 15 µm and/or a $d_{98}(vol)$ of from 2 to 150 µm, preferably from 5 to 120 µm, more preferably from 8 to 80 µm, and most preferably from 10 to 30 µm.

Surface-reacted calcium carbonate and the catalyst obtainable by calcination of said calcium carbonate can be in the form of a loose powder. However, the catalyst can also be in a compacted from, e.g. in the form of a granulate, a pellet, a tablet or an extrudate which can be formed either by compaction of the catalyst precursor (i.e. non-calcined surface-reacted calcium carbonate) or by compaction of the activated catalyst (i.e. calcined surface-reacted calcium carbonate). The compacted forms can be advantageous for the separation of the catalyst from the reaction mixture.

The skilled person will recognize that the particle size distribution and/or the specific surface area of the catalyst can be controlled by applying the appropriate calcination temperature and/or calcination time. In a further embodiment, the catalyst is thus obtainable by calcination of surface-reacted calcium carbonate, wherein the calcination temperature and the calcination time are such that the catalyst has a $d_{50}(vol)$ of from 1 to 75 μm, preferably from 1.5 to 50 μm, more preferably from 2 to 30 μm, and most preferably from 3 to 15 μm and/or a $d_{98}(vol)$ of from 2 to 150 μm, preferably from 5 to 120 μm, more preferably from 8 to 80 μm, and most preferably from 10 to 30 μm and/or a specific surface area of from 1 to 200 $m^2/g$, preferably from 5 to 120 $m^2/g$, and most preferably from 10 to 100 $m^2/g$, measured using nitrogen and the BET method according to ISO 9277:2010. In any of these embodiments, the calcination temperature can be at least 650° C., preferably at least 680° C., and most preferably from 700 to 950° C. and/or the calcination time can be at least 5 min, preferably at least 0.25 hours, more preferably at least 0.5 hours, and most preferably from 1 to 3 hours, for example calcination can be carried out at 700 to 950° C. for 1 to 3 hours.

In general, the catalyst of the present invention is defined such that it comprises calcined surface-reacted calcium carbonate. However, as explained hereinabove, the term "consisting of" is considered to be a preferred embodiment of the term "comprising" and therefore, any aspect and embodiment disclosed in this document equally refers to a catalyst consisting of calcined surface-reacted calcium carbonate.

(D) Transesterification Step

In step (d) of the inventive method, the substrate provided in step (a) and the first alcohol provided in step (b) are reacted in the presence of the catalyst provided in step (c) to obtain a reaction mixture comprising a second carboxylic acid ester and a second alcohol.

As explained in the introductory part, the reaction in step (d) is a transesterification that can be illustrated by the following reaction scheme:

$$R''O(O{=}\!)CR + R'OH \rightarrow R'O(O{=}\!)CR + R''OH$$

in view of which the skilled person will recognize that R' and R" structurally different radicals. However, R can be the same or a different radical as R' or R".

Therefore, the method according to the present invention can be described by the following steps:

(a) providing a substrate comprising a first carboxylic acid ester R"O(O=)CR;
(b) providing a first alcohol R'OH;
(c) providing a catalyst; and
(d) reacting the substrate provided in step (a) and the first alcohol provided in step (b) in the presence of the catalyst provided in step (c) to obtain a reaction mixture comprising a second carboxylic acid ester R'O(O=)CR and a second alcohol R"OH;
characterized in that the catalyst comprises calcined surface-reacted calcium carbonate, wherein the surface-reacted calcium carbonate is a reaction product of ground natural calcium carbonate-containing mineral (GNCC) or precipitated calcium carbonate (PCC) with carbon dioxide and one or more $H_3O^+$ ion donors, wherein the carbon dioxide is formed in situ by the $H_3O^+$ ion donors treatment and/or is supplied from an external source, and wherein R' and R" are structurally different organic radicals.

The inventors have found that a calcined surface-reacted calcium carbonate is able to catalyze the transesterification reaction illustrated above.

The catalyst can be applied in the inventive method at various concentrations. In one embodiment, the catalyst is used in step (d) of the inventive method in an amount of from 0.01 to 20 wt. %, preferably from 0.1 to 10 wt. %, and most preferably from 0.5 to 5 wt. %, based on the total weight of the substrate.

In order to improve the total conversion or the reaction rate, it may be beneficial if the first alcohol is used in molar excess relative to the first carboxylic acid ester contained in the substrate. Therefore, in one embodiment, the first alcohol provided in step (a) is used as reaction medium in step (d) of the inventive method, preferably the first alcohol is used in molar excess relative to the first carboxylic acid ester. More preferably, the alcohol is used as reaction medium in step (d), wherein the molar ratio of the first carboxylic acid ester and the first alcohol is at least 1:1.5, preferably at least 1:2, more preferably at least 1:3, and most preferably at least 1:5.

The transesterification step can be carried out at ambient temperature or, more preferably, at elevated temperature, wherein the reaction mixture should be in a liquid state allowing for adequate stirring. In one embodiment, step (d) is carried out at a temperature of at least 20° C., preferably at least 25° C., and most preferably at a range of from 30 to 80° C. In still another embodiment, step (d) is carried out at a temperature of from 40 to 60° C. The reaction temperature can be adjusted in order to control the total conversion and the reaction rate.

In many cases, it is appropriate to adjust the reaction temperature to a temperature that is closely below the boiling point of the reaction mixture, or the reaction mixture is heated under reflux. In case the first alcohol is used as the reaction medium in step (d), it can be preferred that the reaction temperature in step (d) is closely below the boiling point of said alcohol. Therefore, in a preferred embodiment, the substrate and the first alcohol are reacted in step (d) at a temperature that is from 25 to 5° C. below the boiling point of said alcohol under the given conditions. For example, if methanol is used as the reaction medium at ambient pressure, the reaction temperature can be in a range of from 40 to 60° C. In a particularly preferred embodiment, the first alcohol is a monohydric alcohol as defined hereinabove, wherein said first alcohol is used as reaction medium in step (d), preferably the molar ratio of the first carboxylic acid ester and said first alcohol is at least 1:1.5, more preferably at least 1:2, still more preferably at least 1:3 and most preferably at least 1:5, and wherein the substrate and the first alcohol are reacted in step (d) at a temperature that is from 25 to 5° C. below the boiling point of said alcohol under the given conditions.

In still another embodiment, transesterification step (d) is carried out at ambient pressure or at increased pressure, preferably at ambient pressure. While it is more convenient to carry out the inventive method under ambient pressure, increased pressure may allow for higher reaction temperatures and higher reaction rates. In still another embodiment according to the present invention, step (d) is carried out under an inert gas atmosphere, wherein preferred inert gases are nitrogen, argon and mixtures thereof.

Independently from whether the first alcohol is used in molar excess relative to the first ester, an inert solvent can be used in step (d) of the inventive method that may act as a co-solvent and may be beneficial to control the total conversion or the reaction rate. In the present case, inert means that the solvent is inert under the conditions applied in step (d) of the inventive method. Preferred examples include polar aprotic solvents, such as acetonitrile, dimethylformamide or dimethylsulfoxide.

In principle, the reaction mixture of step (d) can be prepared by mixing each of the components (first carboxylic acid ester, first alcohol and catalyst) in any conceivable order, and in one or more portions. However, to ensure adequate mixing and pre-conditioning, it can be preferred, in one embodiment of the invention, that the alcohol, the catalyst and the optional co-solvent are contacted and pre-mixed in a first step and the substrate is then added in a second step.

Although the present invention shall not be understood as being limited to specific combinations, some exemplary advantageous embodiments will be disclosed in the following:

In one exemplary embodiment, the substrate is a fat or a fatty oil, preferably a fatty oil, wherein the first alcohol is a monohydric alcohol, preferably selected from n-propyl alcohol, isopropyl alcohol, ethanol and methanol, still more preferably methanol or ethanol, and most preferably said first alcohol is methanol.

In another exemplary embodiment, the substrate is a fat or a fatty oil, preferably a fatty oil, wherein the first alcohol is a monohydric alcohol, preferably selected from n-propyl alcohol, isopropyl alcohol, ethanol and methanol, still more preferably methanol or ethanol, and most preferably said first alcohol is methanol, wherein the catalyst is obtainable by calcination of surface-reacted calcium carbonate at a calcination temperature of at least 650° C., preferably at least 680° C., and most preferably at a temperature of from 700 to 950° C., and/or at a calcination time of at least 5 min, preferably at least 0.25 hours, more preferably at least 0.5 hours, and most preferably at a calcination time of from 1 to 3 hours.

In another exemplary embodiment, the substrate is a fat or a fatty oil, preferably a fatty oil, wherein the first alcohol is a monohydric alcohol, preferably selected from n-propyl alcohol, isopropyl alcohol, ethanol and methanol, still more preferably methanol or ethanol, and most preferably said first alcohol is methanol, wherein the catalyst is obtainable by calcination of surface-reacted calcium carbonate, wherein the calcination temperature and the calcination time are such that the catalyst has a $d_{50}$(vol) of from 1 to 75 μm, preferably from 1.5 to 50 μm, more preferably from 2 to 30 μm, and most preferably from 3 to 15 μm and/or a $d_{98}$(vol) of from 2 to 150 μm, preferably from 5 to 120 μm, more preferably from 8 to 80 μm, and most preferably from 10 to 30 μm and/or a specific surface area of from 1 to 200 m²/g, preferably from 5 to 120 m²/g, and most preferably from 10 to 100 m²/g, measured using nitrogen and the BET method according to ISO 9277:2010.

In any of the foregoing exemplary embodiments, the catalyst can be used in transesterification step (d) of the inventive method in an amount of from 0.01 to 20 wt. %, preferably from 0.1 to 10 wt. %, and most preferably from 0.5 to 5 wt. %, based on the total weight of the substrate.

Furthermore, in any of the foregoing exemplary embodiments, said first alcohol can be used as reaction medium in step (d), wherein preferably the molar ratio of the first carboxylic acid ester and the first alcohol is at least 1:1.5, more preferably at least 1:2, still more preferably at least 1:3, and most preferably at least 1:5 and/or the substrate and the first alcohol are reacted in step (d) at a temperature that is from 25 to 5° C. below the boiling point of said first alcohol under the given conditions.

(E) Optional Steps and Further Aspects

It is noted that, where appropriate, the details and embodiments disclosed in the previous sections equally apply to any further aspects and embodiments disclosed in the following.

In step (d) of the inventive process, a reaction mixture is obtained which comprises a second carboxylic acid ester and a second alcohol.

Further, the obtained reaction mixture usually comprises residual catalyst. In one embodiment, the method of the present invention thus further comprises step (e) of separating residual catalyst contained in the reaction mixture of step (d), preferably by filtration.

In another embodiment, the process of the present invention further comprises step (f) of separating said second carboxylic acid ester from said second alcohol contained in the reaction mixture of step (d). For this purpose, any method known to the skilled person can be used, for example, liquid phase separation, extraction, evaporation or fractional distillation. As noted hereinabove, the substrate can comprise a mixture of two or more structurally different carboxylic acid esters, e.g. different triglycerides as in case of natural fats. In turn, a polyesterified polyhydric alcohol, such as a triglyceride, can be substituted with different acyl radicals. In each of these cases, a mixture of two or more structurally different esters can be obtained, all of which representing second carboxylic acid esters in the meaning of the present invention.

In many cases, liquid phase separation can be the method of choice for the separation of the main products, i.e. carboxylic acid esters and alcohols. Typically, the heavy or polar phase contains the alcohol product obtained in transesterification step (d) together with unreacted or excess alcohol provided in step (a). The lighter or non-polar phase usually contains the ester product. For example, if the substrate provided in step (a) is a fat, such as a fatty oil, the carboxylic acid ester is a triglyceride that leads to the formation of one or more fatty acid esters and glycerine which can be separated by said liquid phase separation, for example in a separatory funnel. Water or brine can be used to improve phase separation and to remove water-soluble impurities contained in the ester phase.

As noted above, a particularly preferred embodiment uses a triglyceride-containing substrate, such as vegetable oil, that is provided in step (a) and methanol that is provided as the first alcohol in step (b). In this case, a mixture of structurally different fatty acid esters (FAMEs) is obtained, all of which representing second carboxylic acid esters in the meaning of the present invention.

Depending on the separation method, it is possible to conduct the method as a batch process or as an continuous process.

The carboxylic acid esters obtainable by the inventive process, in particular those obtained from fat-based substrates such as vegetable oil, are valuable fuels and represent a non-fossil alternative energy source that can be used either alone or as a fuel component.

Therefore, one further aspect of the present invention relates to the use of the inventive method in the production of fuel or fuel components.

Especially the vegetable or animal fat-based esters obtained by the inventive method can be used as fuel or as fuel component and can be referred to as biodiesel. Thus, according to further aspects, the present invention relates to a carboxylic acid ester obtainable by the inventive method disclosed herein and to its use as fuel or as a fuel component.

Another product obtained by the inventive process is the second alcohol which is structurally derived from the ester of the substrate. As mentioned above, the inventors have found that the use of the inventive catalyst leads to a reduction of impurities, especially in the alcohol product and in particular in cases where the second alcohol is glycerine.

Still another aspect of the present invention thus relates to an alcohol obtainable by the inventive method. A preferred aspect in this regard refers to glycerine obtainable by the inventive method, for example if the substrate contains glycerides as in case of the fat-based substrates disclosed hereinabove.

Finally, further aspects of the present invention relate to a transesterification catalyst comprising calcined surface-reacted calcium carbonate and to its use as a catalyst in transesterification reactions. Reference is made to the details and embodiments relating to the catalyst used in the inventive process as disclosed in Section (C).

EXAMPLES

The scope and interest of the invention may be better understood on basis of the following examples which are intended to illustrate embodiments of the present invention.

(A) ANALYTICAL METHODS

All parameters defined throughout the present document and those mentioned in the following examples are based on the following measuring methods:

Particle Size Distribution

For determining the volume-based particle size distribution, a Malvern Mastersizer 2 000 Laser Diffraction System is used. The raw data obtained by the measurement are analysed using the Fraunhofer theory and Malvern Application Software 5.60. In general, the measurement is performed with an aqueous dispersion with the exception of the calcined surface-reacted calcium carbonate which was measured in dry state (<0.5 wt. % total moisture based on the total weight of the sample) and at a pressure of 400 kPa. The weight determined particle size distribution may correspond to the volume determined particle size if the density of all the particles is equal.

Any weight-based particle size distribution is measured by the sedimentation method, which is an analysis of sedimentation behaviour in a gravimetric field. The measurement was made with a Sedigraph™ 5120 from Micromeritics Instrument Corporation, USA. The method and the instrument are known to the skilled person and are commonly used to determine particle size distributions of e.g. fillers and pigments. The measurement was carried out in an aqueous solution of 0.1 wt.-% $Na_4P_2O_7$. The samples were dispersed using a high speed stirrer and supersonicated.

X-Ray Diffraction (XRD)

XRD experiments are performed on the samples using rotatable PMMA holder rings. Samples are analysed with a Bruker D8 Advance powder diffractometer obeying Bragg's law. This diffractometer consists of a 2.2 kW X-ray tube, a sample holder, a $\vartheta$-$\vartheta$ goniometer, and a VANTEC-1 detector. Nickel-filtered Cu K$\alpha$ radiation is employed in all experiments. The profiles are chart recorded automatically using a scan speed of 0.7° per min in 2$\vartheta$. The resulting powder diffraction pattern can easily be classified by mineral content using the DIFFRACsuite software packages EVA and SEARCH, based on reference patterns of the ICDD PDF 2 database.

Quantitative analysis of diffraction data refers to the determination of amounts of different phases in a multi-phase sample and has been performed using the DIFFRACsuite software package TOPAS. In detail, quantitative analysis allows to determine structural characteristics and phase proportions with quantifiable numerical precision from the experimental data itself. This involves modeling the full diffraction pattern using the Rietveld approach such that the calculated pattern(s) duplicates the experimental one.

Unless indicated otherwise, activated solids were stored temporarily in round bottom flask purged with an inert atmosphere (e.g. $N_2$) until the XRD measurement is performed.

Specific Surface Area

The specific surface area (in $m^2/g$) of surface-reacted calcium carbonate or other materials is determined using the BET method (using nitrogen as adsorbing gas), which is well known to the skilled man (ISO 9277:2010). The total surface area (in $m^2$) can be obtained by multiplication of the specific surface area and the mass (in g) of the corresponding sample. For performing the measurement on thermally activated solids, similar precautions were taken as described above for X-ray diffraction.

Scanning Electron Microscope (SEM)

The SEM images were produced by using the field emission scanning electron microscope (FESEM) Zeiss Sigma VP from Carl Zeiss Microscopy GmbH, Jena, Germany.

Nuclear Magnetic Resonance Spectroscopy (NMR Spectroscopy)

Samples were characterized using a Bruker 300 MHz Spectrometer Avance 300. Specific weights of samples were solubilized in dichloromethane-$d_2$, prior to the analyses.

(B) EXAMPLES

The following examples are not to be construed to limit the scope of the claims in any manner whatsoever.

Comparative Example 1—CE1

A first comparative trial was carried out in a 250 mL round bottom flask using a commercial sunflower oil (M Classic sun flower oil from Migros) using anhydrous methanol (for HPLC, >99.9% from Sigma Aldrich) and NaOH pellets (ACS reagent>97% from Sigma Aldrich) as a homogeneous base catalyst. In this process, an oil/methanol weight ratio of 2:1 was used and an oil/NaOH weight ratio of 170:1, was employed. First, anhydrous methanol was mixed with NaOH pellets at 30° C. for 30 minutes. At the same time, in another round bottom flask, the vegetable oil was also heated at 30° C., after 30 minutes the vegetable oil was added to the methanol/NaOH mixture, dropwise. Further, the temperature was increased gradually to 50° C. In the end of the addition, the temperature of the whole mixture was increased to 60° C. and kept for a duration of 2 to 3 hours.

Figure 1:
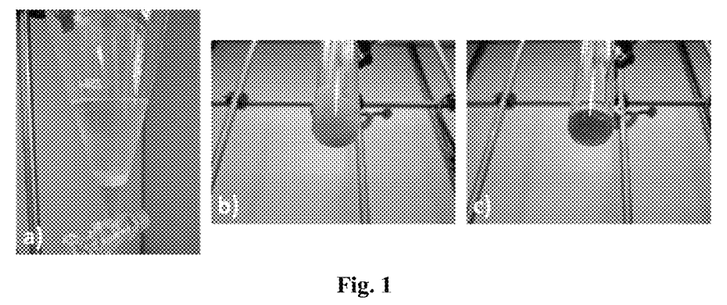
FIG. 1: (a) Phase separation after the transesterification process; (b) Crude glycerol obtained using NaOH as a catalyst; (c) Crude glycerol obtained using KOH as a catalyst.

In the end of the process, the reaction was stopped, methanol was evaporated under vacuum at 50° C./25 mbar for a ca. time of 15 to 20 min. Finally, the mixture was transferred into a separatory funnel, in order to separate the obtained phases (see FIG. 1a). The upper lighter phase corresponds to the transesterification product, the heavy lower phase contains the crude glycerol.

Comparative Example 2—CE2

An analogous catalytic evaluation as for CE1 was performed by using KOH as a base source, wherein the oil/KOH weight ratio was 119:1.

Comparative Example 3—CE3

Preparation and Activation of the Catalyst

A conventional ground natural calcium carbonate (GNCC) was obtained via wet grinding and spray drying of Carrara marble. The ground calcium carbonate had a specific surface area of 4 m$^2$/g and a d$_{50}$(wt) of 1.6 μm.

Figure 2:
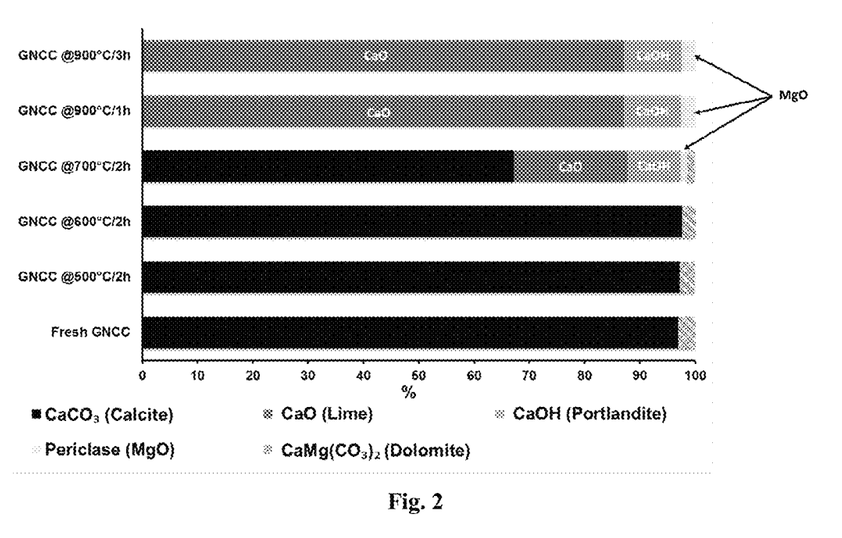
FIG. 2: X-ray diffractograms of ground natural calcium carbonate activated thermally at different temperatures and different times of thermal activation.

The ground calcium carbonate was calcined for the purpose of catalyst activation. Different thermal activation conditions (i.e. temperatures and time of activation) were employed. After activation, the solids were next characterised using X-ray diffraction (XRD) as well as using BET techniques and SEM imaging (see FIG. 2, FIG. 3 and FIG. 6). Using the latter two techniques, an idea about the chemical composition and surface of the solids is provided.

The thermal activation of GNCC at different temperatures showed that a thermal treatment of at least 700° C. is preferred to achieve full calcination. Further, the results show e.g. a clear increase of the surface area from 4 m$^2$/g to 14 m$^2$/g and the formation of micropores for the mineral activated at 900° C. for 2 hours.

Heterogeneous Catalysis Trials

The transesterification carried out with this the heterogeneous catalyst is analogous to the protocol presented in CE1.

0.75 g of the activated catalyst prepared above were placed in a three-neck bottom flask, then purged with N$_2$ for about 10 min. 25 g of anhydrous methanol were added to the catalyst, stirred, then again the system was purged with N$_2$ to eliminate any air traces. The mixture was heated up to 30° C. and stirred for 30 min. 50 g of sun flower oil (M Classic sun flower oil from Migros) were heated in another round-bottom flask at 30° C. for 30 min. After 30 min, the heated oil was added to the catalyst/methanol mixture and then the mixture was progressively heated to 50° C. In the end of the addition, the whole mixture catalyst/methanol/vegetable oil was heated to 60° C. and kept at that temperature 2 to 3 hours. In the end of the process, methanol was evaporated under vacuum at a temperature of 50° C./25 mbar for about 15 to 20 min. Then the solid was separated by a filtration using a Whatman filter paper of a 589/1 grade.

Inventive Example—EX1

Preparation and Activation of the Catalyst

In an exemplary trial, a surface-reacted calcium carbonate (SRCC) was obtained as follows: 10 litres of an aqueous suspension of ground marble were prepared in a mixing vessel by adjusting the solids content to 10 wt. %, based on the total weight of the aqueous suspension. The ground marble was obtained from Hustadmarmor, Norway and had d$_{90}$(wt) of less than 2 μm. An aqueous solution was prepared which contained 30 wt. % of phosphoric acid while another solution was prepared which contained 5 wt. % of citric acid. Whilst mixing the suspension, 1.60 kg of the phosphoric acid solution were added to said suspension over a period of 10 min and at a temperature of 70° C. Additionally, starting 2 min after the start of phosphoric acid addition, 0.05 kg of the citric acid solution were added to the slurry. Finally, after the addition of the phosphoric acid, the slurry was stirred for another 5 min before removing it from the vessel. The obtained solid was then filtered and dried.

An analogously prepared surface-reacted calcium carbonate having a specific surface area of 135 m$^2$/g, a d$_{50}$(vol) of 6.2 μm and a d$_{98}$(vol) of 12.8 μm was used in the following trials.

The surface-reacted calcium carbonate (SRCC) was calcined for the purpose of catalyst activation. Different thermal activation conditions (i.e. temperatures and time of activation) were employed. After activation, the solids were next characterised using X-ray diffraction (XRD) as well as using BET techniques and SEM imaging (see FIG. 3, FIG. 4 and FIG. 5).

The thermal activation of GNCC at different temperatures showed that a thermal treatment of at least 700° C. is preferred to achieve the desired activity. As becomes apparent from FIG. 3, the surface area of the surface-reacted calcium carbonate as a function of temperature is in stark contrast to that of ground natural calcium carbonate, as its surface area decreased in function of the thermal activation conditions. Indeed, the surface area decreased from 135 m$^2$/g in the fresh sample to 15 m$^2$/g after activation for 2 hours at 900° C. However, as can be gathered from FIG. 5, the surface structure of the calcined surface-reacted calcium carbonate (SRCC) is comparable to that of the surface-reacted calcium carbonate prior to calcination.

Heterogeneous Catalysis Trials

An identical procedure as described in CE3 was used in the trials with the catalyst prepared from surface-reacted calcium carbonate.

(C) EVALUATION OF CATALYST PERFORMANCE

Where indicated in the following, all yields of transesterification products were calculated based on $^1$H-NMR spectra and normalised.

Homogeneous Catalysts

Using either NaOH or KOH, the presence of transesterification product was confirmed using proton nuclear magnetic resonance ($^1$H-NMR), since no vegetable oil signals were observed which confirms its full conversion. The high yields of transesterification products were also confirmed by certified analyses according to EN 14103. A difference could be observed in the physical appearance of the crude glycerol. In case of NaOH, the crude glycerol is less viscous compared to a more viscous crude glycerol obtained in case of KOH (see FIG. 1b and FIG. 1c).

Heterogeneous Catalysts

The evaluation of calcined GNCC as transesterification catalyst showed that the catalysts activated at temperatures above 700° C. were more efficient as full conversion could be observed in this case.

The performance of calcined SRCC as transesterification catalyst was investigated in an analogous manner. The analysis revealed that full conversion was possible with SRCC activated at 900° C. and 700° C., respectively.

The comparison in catalytic performance of calcined GNCC and calcined SRCC can be summarized as follows:

| Type of catalyst | Activation conditions | Transesterification rate (%) |
| --- | --- | --- |
| GNCC | 900° C./1 h | ~98 |
| GNCC | 700° C./1 h | ~98 |
| GNCC | 600° C./1 h | traces |
| GNCC | 500° C./1 h | none |
| SRCC | 900° C./1 h | ~98 |
| SRCC | 700° C./1 h | ~98 |
| SRCC | 600° C./1 h | traces |
| SRCC | 500° C./1 h | none |

The comparison of calcined GNCC and calcined SRCC shows that SRCC, surprisingly, performs equally well although the specific surface area is decreased during activation and the lime (CaO) content is comparably low.

Figure 8:
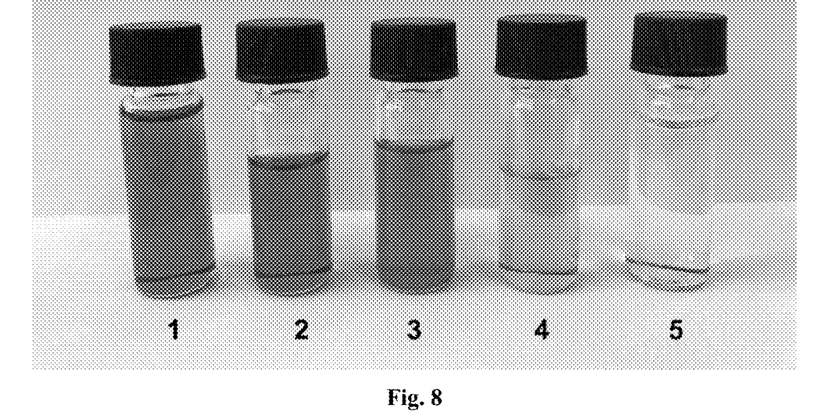
FIG. 8: Crude glycerol obtained by using: 1) KOH, 2) NaOH, 3) calcined GNCC and 4) calcined SRCC as catalysts, 5) is pure glycerol.

Furthermore, a comparison of the crude glycerol phases shows that the glycerol obtained by using calcined SRCC is clearer than the one obtained using calcined GNCC or conventional catalysts (see FIG. 8). This fact suggests that the crude glycerol obtained by using calcined SRCC has a higher purity grade than the one obtained by using the calcined GNCC or NaOH/KOH.

The invention claimed is:

1. A transesterification catalyst comprising partially or fully calcined surface-reacted calcium carbonate, wherein the calcination is carried out at a calcination temperature of at least 650° C.,
   wherein the transesterification catalyst has a specific surface area of from 15 to 200 m$^2$/g, measured using nitrogen and the BET method according to ISO 9277:2010, and
   wherein the surface-reacted calcium carbonate is a reaction product of ground natural calcium carbonate containing mineral (GNCC) or precipitated calcium carbonate (PCC) with carbon dioxide and one or more $H_3O^+$ ion donors and wherein the carbon dioxide is formed in situ by a reaction with the $H_3O^+$ ion donors and/or is supplied from an external source, and
   wherein the surface-reacted calcium carbonate has a specific surface area of from 15 to 200 m$^2$/g, measured using nitrogen and the BET method according to ISO 9277:2010.

2. The transesterification catalyst according to claim 1, characterized in that the transesterification catalyst has:
   (i) a $d_{50}$(vol) of from 1 to 75 μm; and/or
   (ii) a $d_{98}$(vol) of from 2 to 150 μm.

3. The transesterification catalyst according to claim 1, characterized in that the transesterification catalyst has:
   (i) a $d_{50}$(vol) of from 3 to 15 μm; and/or
   (ii) a $d_{98}$(vol) of 10 to 30 μm.

4. The transesterification catalyst according to claim 1, characterized in that the transesterification catalyst has a specific surface area of from 25 to 180 m$^2$/g, measured using nitrogen and the BET method according to ISO 9277:2010.

5. The transesterification catalyst according to claim 1, characterized in that the transesterification catalyst has a specific surface area of from 30 to 150 m$^2$/g, measured using nitrogen and the BET method according to ISO 9277:2010.

6. A method for transesterification of carboxylic acid esters by heterogeneous catalysis, the method comprising the following steps:
   (a) providing a substrate comprising a first carboxylic acid ester;
   (b) providing a first alcohol;
   (c) providing a catalyst according to claim 1; and
   (d) reacting the substrate provided in step (a) and the first alcohol provided in step (b) in the presence of the catalyst provided in step (c) to obtain a reaction mixture comprising a second carboxylic acid ester and a second alcohol.

7. The method according to claim 6, characterized in that the substrate is a fat or a fatty oil.

8. The method according to claim 6, characterized in that the first carboxylic acid ester is a triglyceride.

9. The method according to claim 6, characterized in that the first alcohol is a monohydric alcohol.

10. The method according to claim 6, characterized in that the surface-reacted calcium carbonate has:
    (i) a $d_{50}$(vol) of from 0.5 to 50 μm; and/or
    (ii) a $d_{98}$(vol) of from 1 to 120 μm.

11. The method according to claim 6, characterized in that the surface-reacted calcium carbonate has a specific surface area of from 25 to 180 m$^2$/g, measured using nitrogen and the BET method according to ISO 9277:2010.

12. The method according to claim 6, characterized in that:
    (i) the ground natural calcium carbonate-containing mineral is selected from the group consisting of marble, chalk, dolomite, limestone and mixtures thereof; and/or
    (ii) the precipitated calcium carbonate comprises aragonitic, vateritic or calcitic mineralogical crystal forms or mixtures thereof.

13. The method according to claim 6, characterized in that the catalyst is obtainable by calcination of surface-reacted calcium carbonate, wherein calcination is carried out:
    (i) at a calcination temperature of at least 680; ° C., and/or
    (ii) at a calcination time of at least 5 mins.

14. The method according to claim 6, characterized in that in step (d):
    the first alcohol is used as reaction medium; and/or
    the catalyst is used in an amount of from 0.01 to 20 wt. %, based on a total weight of the substrate; and/or
    the alcohol and the catalyst are contacted in a first step and the substrate is then added in a second step.

15. The method according to claim 6, characterized in that step (d) is carried out at a temperature of at least 20° C.

16. The method according to claim 6, characterized in that the method further comprises step (e) of separating the second carboxylic acid ester from the reaction mixture obtained in step (d).

17. The method according to claim 6, characterized in that the substrate is a vegetable oil.

18. A method of producing fuel or a fuel component, comprising:
   (a) providing a substrate comprising a first carboxylic acid ester;
   (b) providing a first alcohol;
   (c) providing a catalyst according to claim 1; and
   (d) reacting the substrate provided in step (a) and the first alcohol provided in step (b) in the presence of the catalyst provided in step (c) to obtain a reaction mixture comprising a second carboxylic acid ester and a second alcohol;
   wherein the second carboxylic acid ester is the fuel or fuel component.

* * * * *

UNITED STATES PATENT AND TRADEMARK OFFICE
CERTIFICATE OF CORRECTION

| | | |
|---|---|---|
| PATENT NO. | : 12,006,286 B2 | Page 1 of 1 |
| APPLICATION NO. | : 16/981858 | |
| DATED | : June 11, 2024 | |
| INVENTOR(S) | : Ftouni et al. | |

It is certified that error appears in the above-identified patent and that said Letters Patent is hereby corrected as shown below:

On the Title Page

In the Abstract (57), Delete:
"The present invention relates to a method for transesterification of carboxylic acid esters by heterogeneous catalysis using a catalyst that is obtainable by calcination of surface-reacted calcium carbonate. The invention further relates to the use of said method in the production of fuel or fuel components, such as biodiesel. Further aspects of the present invention relate to the transesterified ester obtainable by the inventive method and to its use as fuel or as fuel component. Still another aspect of the present invention relates to a corresponding transesterification catalyst and to its use in transesterification reactions."

And insert:
--A method for transesterification of carboxylic acid esters by heterogeneous catalysis using a catalyst that is obtainable by calcination of surface-reacted calcium carbonate is disclosed, as is the use of the method in the production of fuel or fuel components, such as biodiesel. The transesterified ester obtainable by the inventive method and its use as fuel or as fuel component is disclosed. A corresponding transesterification catalyst and to its use in transesterification reactions is also disclosed.--

Signed and Sealed this
Twenty-seventh Day of August, 2024

Katherine Kelly Vidal
*Director of the United States Patent and Trademark Office*